United States Patent [19]
Harper et al.

[11] Patent Number: 6,152,934
[45] Date of Patent: Nov. 28, 2000

[54] SURGICAL KNOT TYING INSTRUMENT

[75] Inventors: Kevin A. Harper, Mason, Ohio; Julie D. Dober, Arenzville, Ill.

[73] Assignee: Ethicon Endo-Surgery, Inc., Cincinatti, Ohio

[21] Appl. No.: 09/332,802

[22] Filed: Jun. 14, 1999

[51] Int. Cl.[7] .................................................. A61B 17/00
[52] U.S. Cl. .......................................... 606/139; 606/148
[58] Field of Search .................... 606/139, 144, 606/148, 143, 146, 102, 113

[56] References Cited

U.S. PATENT DOCUMENTS

| | | | |
|---|---|---|---|
| 2,012,776 | 8/1935 | Roeder . | |
| 3,090,386 | 5/1963 | Curtis . | |
| 4,961,741 | 10/1990 | Hayhurst | 606/139 |
| 5,129,912 | 7/1992 | Noda et al. | 606/139 |
| 5,144,961 | 9/1992 | Chen et al. | 128/898 |
| 5,178,629 | 1/1993 | Kammerer | 606/224 |
| 5,201,744 | 4/1993 | Jones | 606/148 |
| 5,211,650 | 5/1993 | Noda | 606/139 |
| 5,234,445 | 8/1993 | Walker et al. | 606/148 |
| 5,314,433 | 5/1994 | Li | 606/139 |
| 5,320,629 | 6/1994 | Noda et al. | 606/139 |
| 5,334,199 | 8/1994 | Yoon | 606/144 |
| 5,336,229 | 8/1994 | Noda | 606/144 |
| 5,391,176 | 2/1995 | de la Torre | 606/148 |
| 5,437,682 | 8/1995 | Grice et al. | 606/148 |
| 5,449,367 | 9/1995 | Kadry | 606/148 |
| 5,454,820 | 10/1995 | Kammerer et al. | 606/148 |
| 5,454,821 | 10/1995 | Harm et al. | 606/148 |
| 5,681,331 | 10/1997 | de la Torre et al. | 606/148 |
| 5,681,332 | 10/1997 | Onuki | 606/148 |
| 5,690,655 | 11/1997 | Hart et al. | 606/148 |
| 5,693,059 | 12/1997 | Yoon | 606/139 |
| 5,792,151 | 8/1998 | Heck et al. | 606/144 |

FOREIGN PATENT DOCUMENTS 2088162  8/1997  Russian Federation .

OTHER PUBLICATIONS

"Cardiac Surgery", (Patricia C. Seifert (1994) Ch. 14 "Aortic Valve Surgery".

Primary Examiner—Michael Buiz
Assistant Examiner—(Vikki) Hoa B. Trinh
Attorney, Agent, or Firm—Dean Garner

[57] ABSTRACT

A surgical instrument is described for tying together the two free ends of a suture placed into the tissue of a surgical patient. The surgical device comprises a handle having an actuator, an elongated shaft attached to the handle, a cartridge, and a pusher. The cartridge removeably attaches to the shaft and comprises a cable with two free cable ends with suture connectors attached thereto. The cable has a plurality of pre-tied loops disposed proximally to the two free cable ends. The pusher is slideably disposed on the shaft and transfers the pre-tied loops from the cable to the two free suture ends of the suture filament. In a preferred embodiment, the pusher comprises a lug train and a driver. The lug train has a plurality of lugs flexibly attached to each other and slideably attached to the distal end of the shaft. When the cartridge is attached to the distal end of the shaft, each of the pre-tied loops is positioned operationally over a corresponding lug. When the actuator is actuated, the driver moves the lug train distally along a top surface of the shaft, around the distal end, and then proximally along a bottom surface of the shaft, whereby the loops are released from the distal end of the instrument.

23 Claims, 15 Drawing Sheets

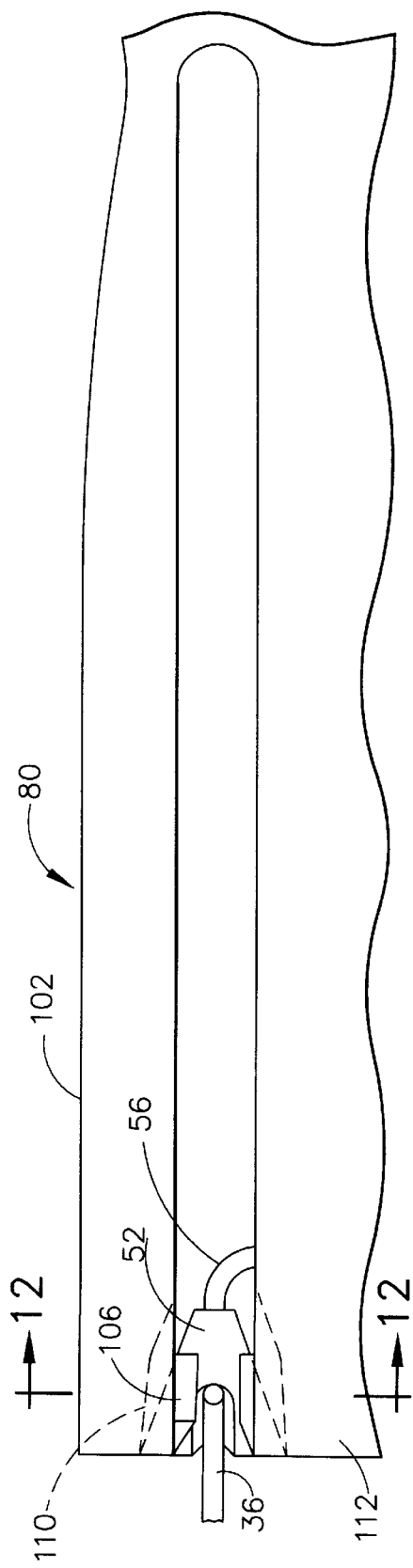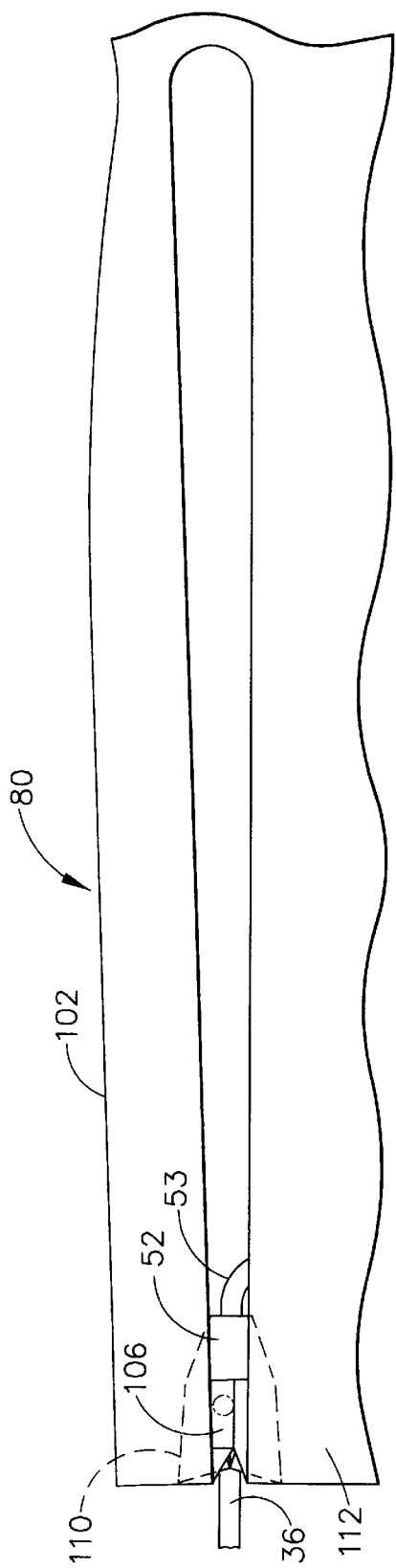

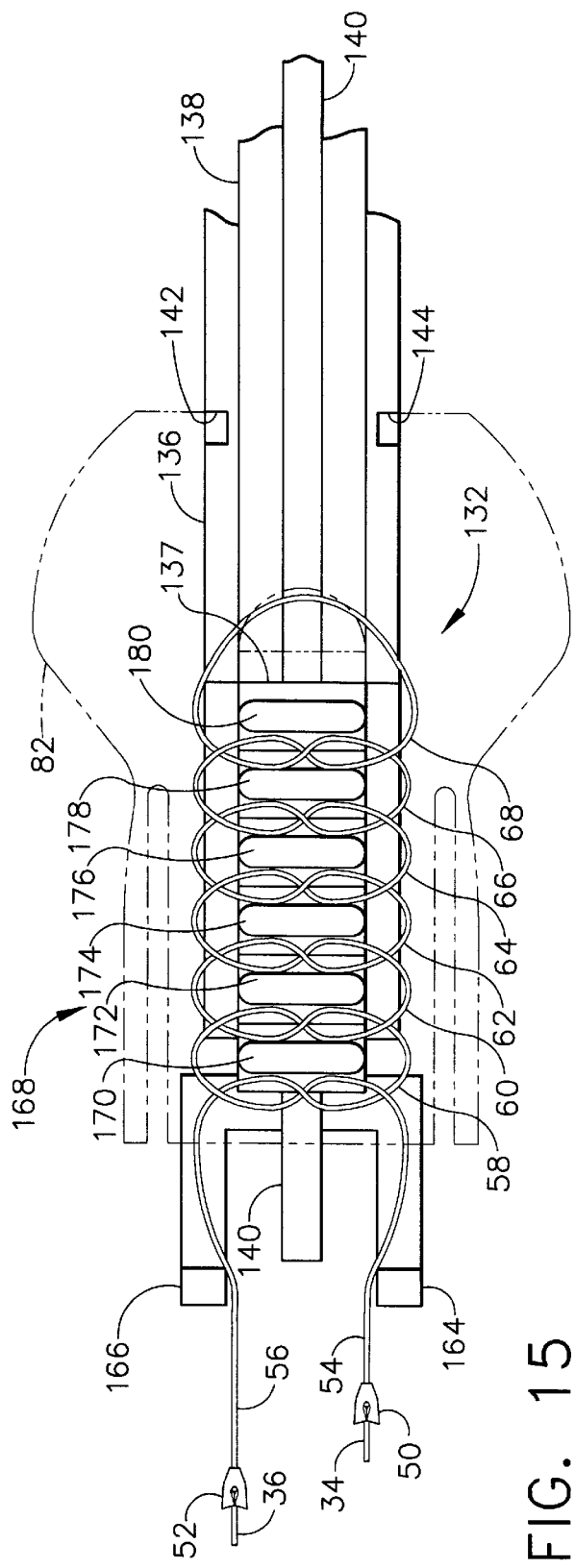
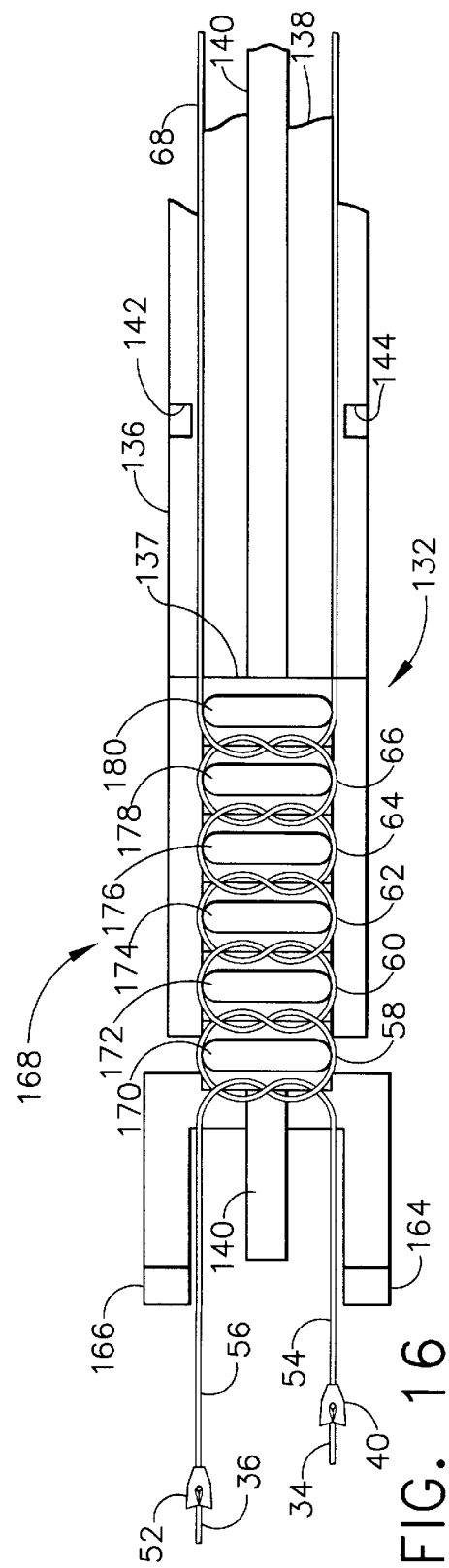
FIG. 15
FIG. 16

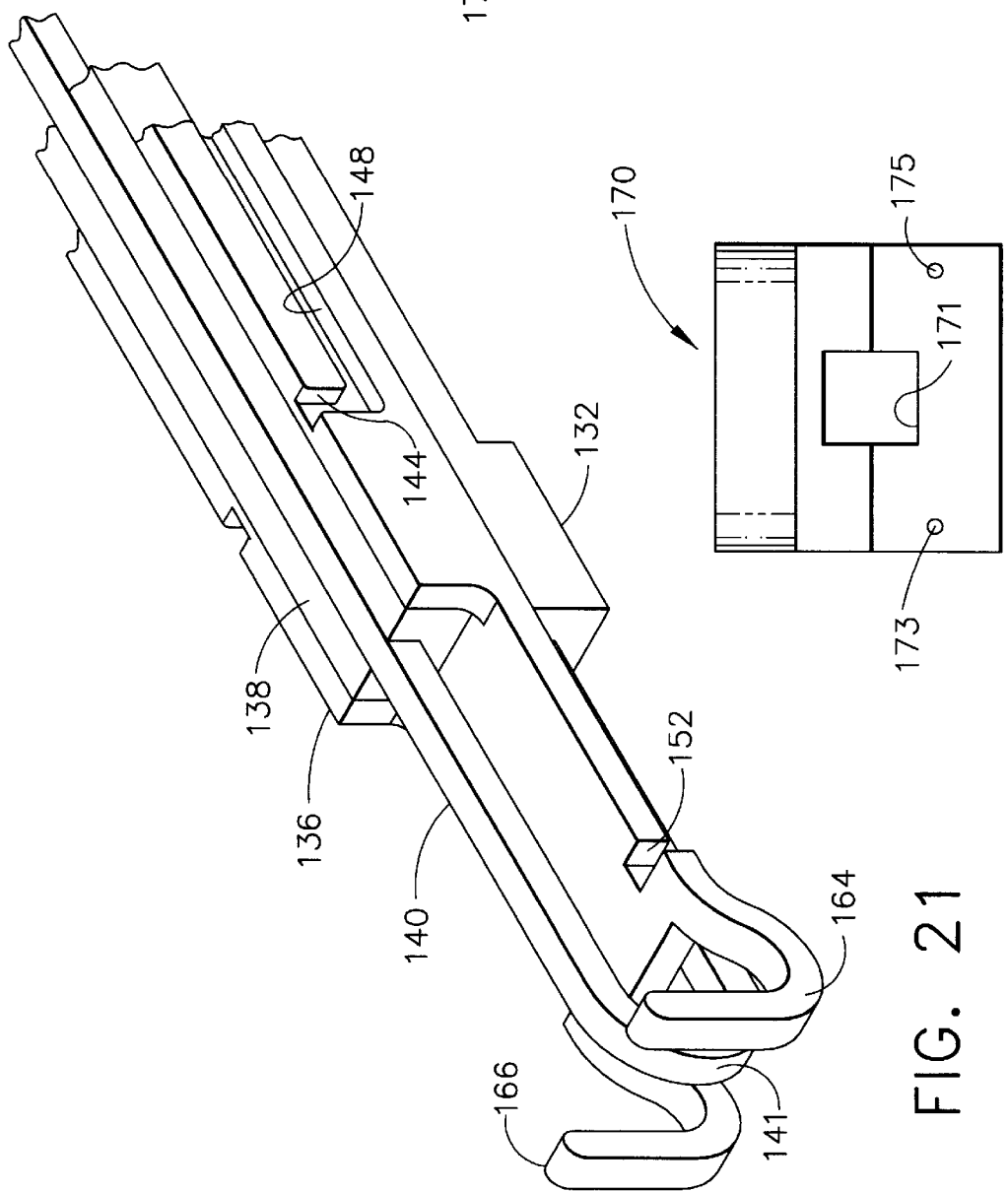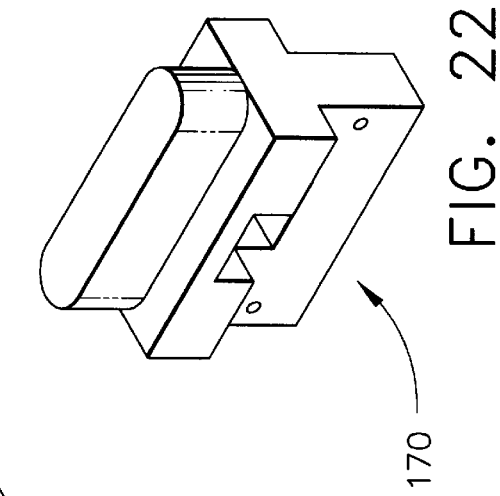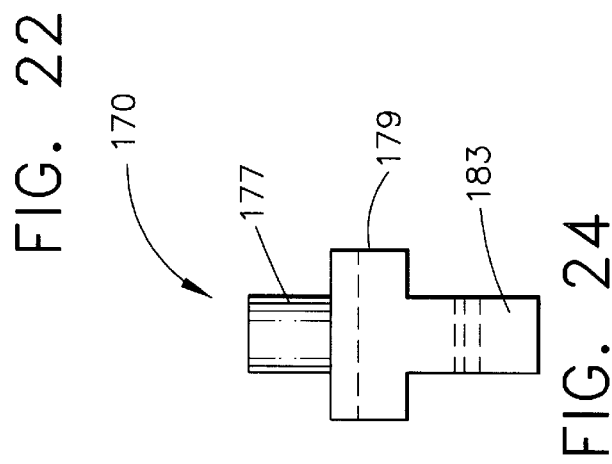

SURGICAL KNOT TYING INSTRUMENT

FIELD OF THE INVENTION

The present invention relates, in general, to a surgical instrument for tying a knot into a suture filament placed into the tissue of a surgical patient. In particular, the invention relates to such a surgical instrument which is adapted for tying the knot during minimally invasive surgical procedures where many surgical knots must be made inside a deep, surgical aperture.

BACKGROUND OF THE INVENTION

The introductions of endoscopic surgical procedures and the newly developed, minimally invasive surgical procedures (those requiring very small incisions in the surgical patient) have brought great attention to the need for surgical instruments to facilitate the placement and securing of suture filaments within the surgical patient. The existing surgical graspers, holders, and passers have allowed surgeons to proceed with certain surgical procedures, even though the time to perform such procedures has been necessarily lengthened. This is due in part to the difficulty in securing the suture filaments. Many types of clips and fasteners have be en developed for securing sutures for maintaining the approximation of the tissue. Nevertheless, surgeons have shown a strong preference for using conventional surgical knots primarily because knots are reliable and do not require implanting foreign materials (other than the suture filament) into the surgical patient.

Certain surgical procedures require the placement of many knots in surgical sites within deep cavities or surgical apertures of the patient. On e such procedure, which is being performed by surgeons throughout the world, is the replacement of diseased and/or dysfunctional heart valves.

The particular valves most often requiring replacement, and for which successful surgical procedures have been developed, include the aortic valve located in the ascending aorta above the left ventricle, and the mitral valve located between the left atrium and the left ventricle of the heart. Healthy valves enable efficient cardiac function by providing unimpeded forward blood flow and preventing backflow into the originating chamber. These valves represent a very complex interplay between the valve leaflets, tendineae, muscles, and heart chamber walls. Unfortunately, the valves of the heart are susceptible to numerous, life-threatening diseases such as stenoses (a narrowing of the valve orifice) and regurgitation (or prolapse, when the valve leaflets do not coapt properly and thus are unable to prevent backflow.)

The trend for all surgical procedures, not only heart valve replacement, is to do the procedure less invasively and more quickly than before. The median sternotomy is still the most widely used means of access to the heart and greater vessels like the aorta. For a median sternotomy, a cut is made through the sternum of the surgical patient's chest, and a retractor is used to forcibly spread the left and right rib cages apart. The newer surgical procedures incorporate an intercostal (between the ribs) approach, also known as a thoracotomy, resulting in a much smaller wound and faster recovery time for the patient. The access, however, to the heart and greater vessels is more difficult with the thoracotomy, and use of the technique has necessitated the development of new surgical devices such as the present invention.

In an aortic valve replacement procedure, an incision is made into the ascending aorta to provide access to the valve. The leaflets of the valve are removed, leaving a thickened portion of the aortic wall known as the annulus. Next a mechanical or biological prosthesis is secured to the natural valve annulus using permanent sutures. Attachment of the prosthesis requires about 12 to 24 interrupted stitches. Each suture filament has a curved needle attached to each of the two free suture ends. A small pledget made from an implantable material is usually placed midway on the suture, and then one of the needles is passed through the valve annulus in a direction perpendicular to the plane of the annulus. The needle may be passed in the bottom-to-top direction so as to be able to view the needle tip piercing through the tissue. The needle may also be passed in the top-to-bottom direction. When both needles of a suture have been placed side-by-side into the annulus as described, the ends are drawn up out of the aorta so that the pledget rests against the tissue as reinforcement. A surgical clamp is normally locked onto the free ends of each pair of sutures and the clamp is then laid on the surgical drape covering the patient. The remaining sutures are likewise placed into the valve annulus, taking care to prevent the sutures from crossing over each other and becoming tangled. When all the sutures have been placed into the valve annulus of the aorta, the array of surgical clamps lying upon the patient serve to keep the sutures organized. Then one-by-one, each clamp is removed and each pair of needles on the respective suture is penetrated through the prosthetic valve. Next, the needles are trimmed off of the ends of the suture and the clamp is again locked onto the suture ends. Once all the sutures have been attached to the prosthesis, it is then "parachuted" into place inside the ascending aorta. Again one-by-one, the clamps are removed and the free ends of each suture pair is tied into a knot against the prosthesis which is at the bottom of the surgical aperture. To make one complete knot, the surgeon must tie one throw (alternating between a right and a left overhand slip knot) at a time, slide it down the suture and against the prosthesis using a fingertip or a knot-pushing device, then repeat the step five more times. The result of these steps is essentially three square knots tied in series. The excess suture is trimmed and the procedure is repeated for the remaining sutures. The time required to secure the sutures as described is a significant portion of the hours required to do the entire surgical procedure. A more detailed description of this surgical procedure may be found in Chapter 14 of *Cardiac Surgery*, Mosby's Perioperative Nursing Series, by Patricia C. Seifert, 1994.

In a busy operating room, there is an unfortunate opportunity for the surgeon to lose track of how many throws have been made when tying knots by hand, or whether the throws have been properly alternated between left and right which is necessary for an optimally secure knot. What is desired for this procedure and other surgical procedures requiring many knots to be placed in deep, surgical apertures, is a surgical device which can attach to two free ends of a suture filament already penetrated into tissue, and to place automatically all the alternating throws for each knot tightly and at the correct location on the surgical site. It is also desired to be able to use the surgical device to help manage the untied suture filaments.

Many devices for tying knots in suture filament within difficult-to-access surgical sites are described in the literature. None of the devices described are able to attach to two free ends of a suture filament already penetrated into tissue, the ends being attached to the device without tying a "pre-tied" knot into the filament, and to quickly and automatically place a secure knot at the surgical site. Several devices are described which have one end of the suture filament pre-tied and mounted on the distal end of the device, the other free end being attached to a needle. Examples are the following: U.S. Pat. No. 5,129,912 issued to Noda, et al on Jul. 14, 1992; U.S. Pat. No. 5,234,445 issued to Walker, et al on Aug. 10, 1993; U.S. Pat. No. 5,391,176 issued to de la Torre on Feb. 21, 1995; U.S. Pat. No. 5,454,820 issued to Kammerer, et al on Oct. 3, 1995; and U.S. Pat. No. 5,454,821 issued to Harm, et al on Oct. 3, 1995.

An instrument for tying and tightening ligature knots is described in a Russian Patent 2088162 to Bersenev, et al, and dated Aug. 27, 1997. This instrument has a coil spring with a single pre-tied loop stored in the hollow, distal end of a shaft. A hook on an end of the coil spring is attached to the suture filaments to be tied together. A pulling mechanism within the shaft is provided for unraveling the spring and transferring the single loop to the suture filaments. An apparent shortcoming of this instrument is the inability to deploy multiple loops into the suture filament in order to create a secure surgical knot similar to what surgeons are able to tie by conventional hand tying techniques. In addition, since the pre-tied loop is pulled through the stationary hollow, distal end of the shaft to transfer the knot to the suture, rather than the pre-tied knot being pushed off the distal end of the instrument, a portion of the tissue is drawn into the distal end of the instrument. This step appears to be traumatic to the tissue being sutured and could result in post-operative complications. What is needed is a way to transfer a pre-tied knot in a coil or equivalent element to the suture filament by pushing (rather than pulling) the pre-tied knot towards the tissue, so that tissue is not drawn into the distal end of the instrument.

SUMMARY OF THE INVENTION

The present invention is a surgical instrument for tying together the two free ends of a suture placed in the tissue of a surgical patient. The present invention may be used in many types of surgical procedures where tissues are approximated using sutures or where it is desired to attach prosthesis to the tissue such as during a heart valve replacement procedure. The present invention is especially useful for surgical procedures requiring the rapid tying of many sutures in succession, and for tying knots in sutures which are placed into tissues within deep surgical apertures, such as the aorta during a heart valve repair procedure. As a result, the time of surgery may be reduced, thus reducing risk to the surgical patient and possibly lowering the cost of the surgical procedure. The present invention allows for methods to be used for managing a plurality of sutures during a procedure, and in general, keeping the sutures from becoming tangled with one another. Finally, the present invention facilitates the formation of a slip-resistant knot in that it provides for the deployment of alternating right and left-hand throws into the suture according to an established surgical technique for knot tying.

The present invention is a surgical instrument comprising a handle having an actuator attached thereto, and an elongated shaft attached to the handle. The instrument further comprises a cartridge removably attached to the shaft. The cartridge has a cable with two free ends with suture connectors attached to thereto, and the cable has a plurality of pre-tied loops disposed proximally to the two free cable ends. The instrument further comprises a pusher slidably disposed on the shaft. The pusher is for transferring the pre-tied loops from the cable to the two free suture ends of the suture filament.

In a preferred embodiment of the present invention, the pusher comprises a lug train and a driver. The lug train has a plurality of lugs equal in number to the plurality of loops of the cable. The lugs are flexibly attached to each other in a row and slidably attached to the distal end of the shaft of the instrument. Each lug has one of the loops of the cable operationally positioned onto it when the cartridge is slidably attached to the shaft. The cartridge also comprises a frame having at least one projection for the slidable insertion into a longitudinal slot of the shaft. When the frame is manually moved from the distal end to the proximal end of the shaft, the loops are transferred from the cable to the two free suture ends of the suture filament.

When the actuator on the handle is actuated, the driver moves the lug train distally along a top surface of the shaft, around the distal end of the shaft, and then proximally along a bottom surface of the shaft. In this way, the loops are released from the distal end of the instrument and tightened simultaneously at the desired location within the surgical patient by the operator pulling the cartridge in the proximal direction while holding the distal end of the shaft against the desired location for the deployed knot.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 10 is a fragmentary top view of the distal right portion of the cartridge of FIG. 1 illustrating the placement of a suture in a slot of one of the pair of suture connectors of FIG. 8.

FIG. 11 is a fragmentary top view of the distal right portion of the cartridge of FIG. 1 illustrating the suture clamped into the suture connector and the distal portion of the suture trimmed off.

FIG. 15 is a top view of the distal end portion of the applicator with the cable assembly in working relationship thereupon, the cartridge shown in phantom for clarity.

FIG. 16 is a top view of the distal end portion of the applicator with the cable loop assembly in working relationship thereupon, after the cartridge has been moved proximally along a longitudinal track of the applicator.

FIG. 21 is an isometric view of the distal end portion of the applicator with the dispensing lugs removed.

FIG. 22 is an isometric view of a dispensing lug of the applicator of FIG. 3.

FIG. 23 is a front view of the dispensing lug of FIG. 22.

FIG. 24 is a side view of the dispensing lug of FIG. 22.

DETAILED DESCRIPTION OF THE INVENTION

Figure 1:
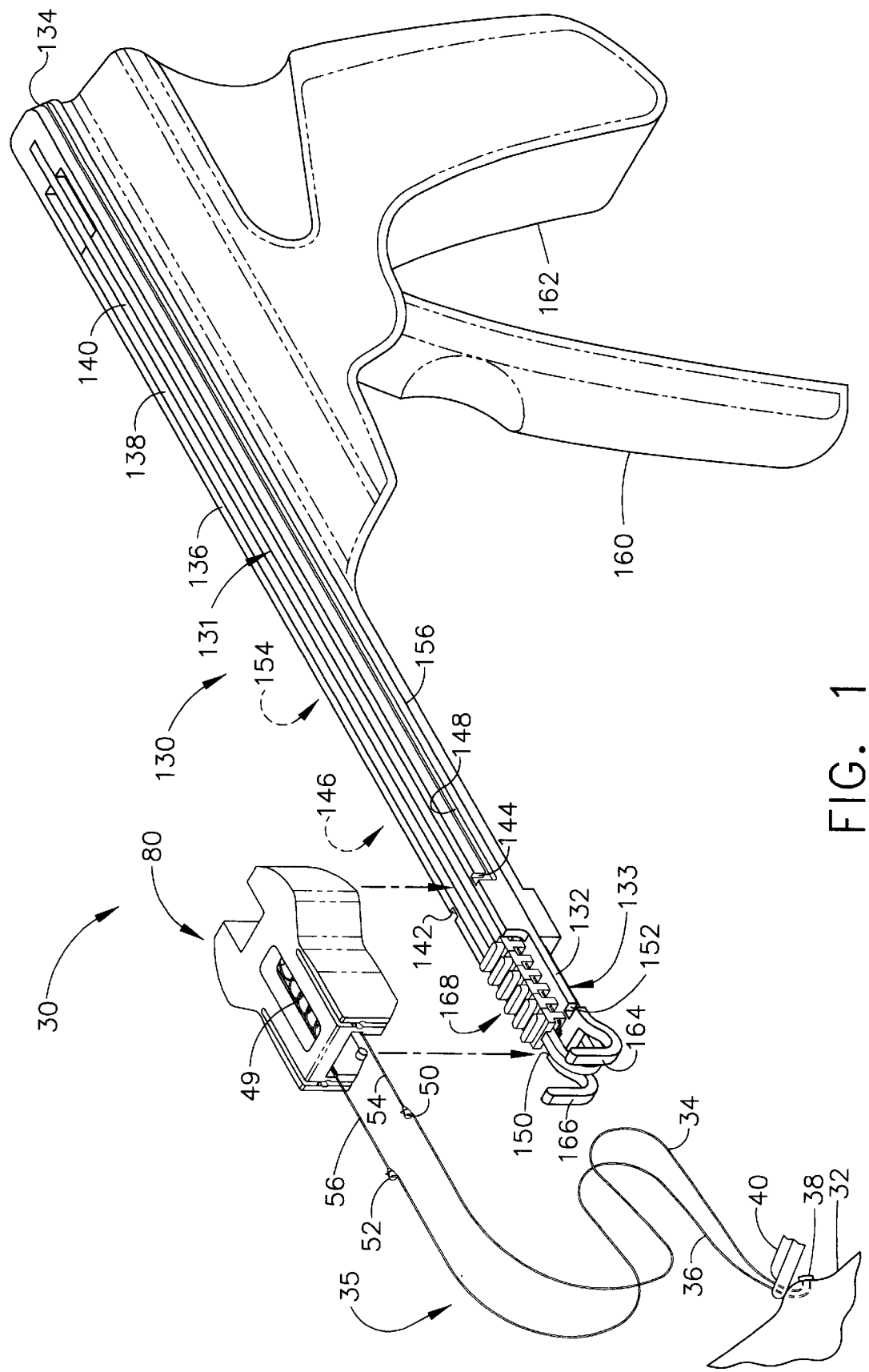
FIG. 1 is an isometric view illustrating the placement of a suture into the distal end slots of a cartridge of the present invention.

A preferred embodiment of the present invention, a surgical knot tying instrument 30, is shown in FIG. 1. The instrument 30 comprises a cartridge 80 and an applicator 130. The steps for using the present invention will be described concurrently with the detailed descriptions of the components. The surgical procedure for which the steps for using the present invention will be described is a heart valve replacement procedure in which prosthesis is attached to the annulus of the interior wall of the aorta. The present invention, however, may be used for other surgical procedures, which require tying the free ends of a suture already placed into the tissue of the surgical patient. The present invention is especially useful for surgical procedures requiring several sutures within deep surgical apertures.

Each cartridge 80 is intended for applying into a suture filament 35 a single surgical knot having a plurality of alternating throws. A plurality of pre-tied loops in a cable loop assembly 49 of the cartridge 80 is transferred to a suture filament 35 already placed through the tissue 32 and the prosthesis 40. Once the surgical knot is deployed, the cartridge 80 may be discarded. The applicator 130 may then be used with a new cartridge 80 containing a cable loop assembly 49. These steps are repeated for each surgical knot that is tied into a suture, one cartridge 80 being used for each surgical knot tied. The artisan will appreciate that the applicator 130 may be made to be either disposable or reusable, depending primarily on the selection of materials of the components.

In FIG. 1 the applicator 130 is shown to comprise a handle 162, an actuator 160, and a shaft 136 attached to the handle 162. The shaft 136 has a distal end 132 and a proximal end 134 with an axis extending therebetween, a left longitudinal slot 148, and a right longitudinal slot 146, upon which the cartridge 80 may slide longitudinally in either the distal or proximal directions. The shaft 136 also has a top surface 131 and a bottom surface 133. In the preferred embodiment shown, the handle 162 is pistol-shaped, but other configurations are possible. The applicator 130 further comprises an upper center rail 140 extending centrally from the proximal to the distal ends of the shaft 136, and an elongated driver 138 slidably disposed beneath the upper center rail 140. The actuator 160 is operationally engaged with the driver 138 so that when the operator squeezes the actuator 160, the driver 138 moves longitudinally in the distal direction. When the operator subsequently releases the actuator 160, the driver 138 moves longitudinally in the proximal direction and returns to its beginning position.

Still referring to FIG. 1, the applicator 130 further comprises a left prong 164 and a right prong 166, both being attached to the distal end of the shaft 136. A lug train 168 is slidably mounted on the upper center rail 140 on the distal end 132 of the applicator 130. As indicated by the arrows, the cartridge 80 is mounted onto the distal end 132 of the track 136 of the applicator 130 directly over the lug train 168. Before doing so, however, the operator must first attach the suture filament 35 to the cable loop assembly 49 of the cartridge 80, according to the steps described next.

Figures 2, 3:
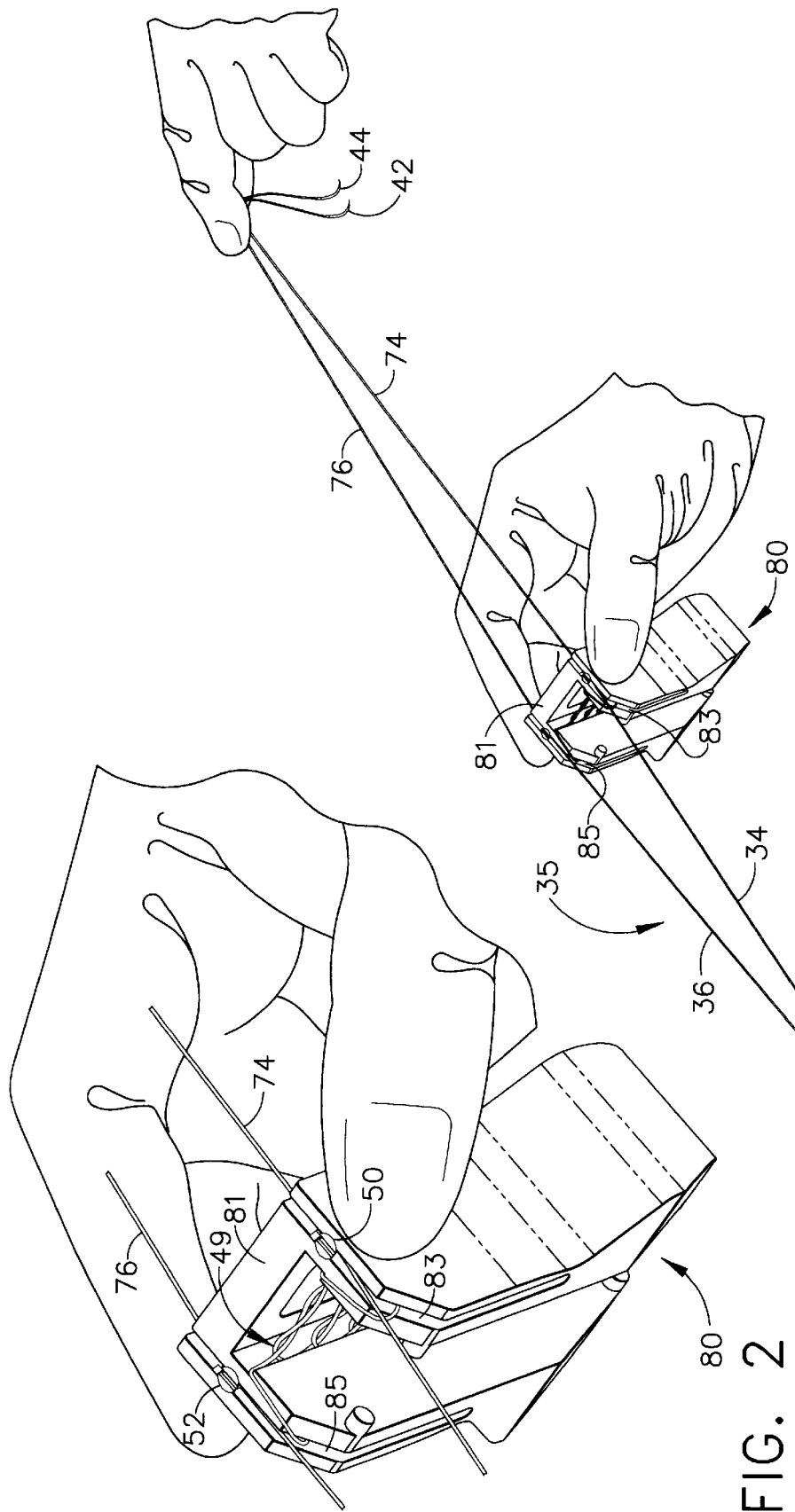
FIG. 2 is an enlarged view of the cartridge of FIG. 1.
FIG. 3 is an isometric view of the cartridge as it is being placed onto the upper distal end of an applicator of the present invention.

In FIGS. 2 and 3, the cartridge 80 is shown as it is held by the right hand of the operator, and the suture filament 35 is aligned with the cartridge 80 by the left hand of the operator for attachment of the suture filament 35 to the cable assembly 49. The suture filament 35 comprises a left suture 34 and a right suture 36 extending from the tissue 32 and prosthesis 40. The suture filament 35 may be made of a conventional suture material such as braided polyester, polypropylene, silk, or from other suture materials commercially available. The diameter of the suture filament 35 which may be used with the present invention is preferably, but not restricted to, a size 2-0 (0.45 mm). FIG. 3 shows that the surgeon has already passed a left needle 42, and a right needle 44, through a pledget 38, the tissue 32, and the prosthesis 40. The left suture 34 and the right suture 36 have been drawn proximally so that they are approximately equal in length. While holding the cartridge 80 with one hand, the operator uses the other hand to align the left and right sutures, 34 and 36, into a left opening 83 and a right opening 85, respectively, on the distal face 81 of the cartridge 80. A left excess suture portion 74 and a right excess suture portion 76 will be trimmed off of the left and right sutures, 34 and 36, respectively, as will be described later. The surgeon then squeezes the cartridge 80 between the thumb and index finger as shown, thus simultaneously attaching the left and right sutures, 34 and 36, to a left connector 50 and a right connector 52, respectively, of the cable loop assembly 49 of the cartridge 80. The left and right connectors, 50 and 52, are attached to a left cable end 54 and a right cable end 56, respectively, both extending from the cable loop assembly 49 housed within the cartridge 80. Once the left and right sutures, 34 and 36, are attached to the left and right connectors, 50 and 52, respectively, the connectors, 50 and 52, may then be gently pulled out of the distal face 81 of the cartridge 80, thus exposing the left and right cable ends, 54 and 56, as shown in FIG. 1. The cartridge 80 may then be laid on top of the surgical drapes covering the patient, and later during the surgical procedure, picked-up and mounted onto the applicator 130 in order to tie a knot into the suture filament 35 to which the cartridge 80 is attached. This may be advantageous to the surgeon, for example, when doing a heart valve surgical procedure where 12–24 knots are to be deployed in order to attach the prosthesis to the aorta. Each of the 12–24 cartridges required is first attached to the sutures as described and then carefully laid onto the surgical drapes covering the chest of the surgical patient in an array so as not to cross the suture filaments. The cartridges, in this way, are very useful for organizing all the 10 sutures. The prosthesis is then "parachuted" into the aorta of the patient. Then one by one, each cartridge is mounted on the applicator 130 and the left and right sutures, 34 and 36, are tied together to hold the prosthesis 40 in place.

Figure 4:
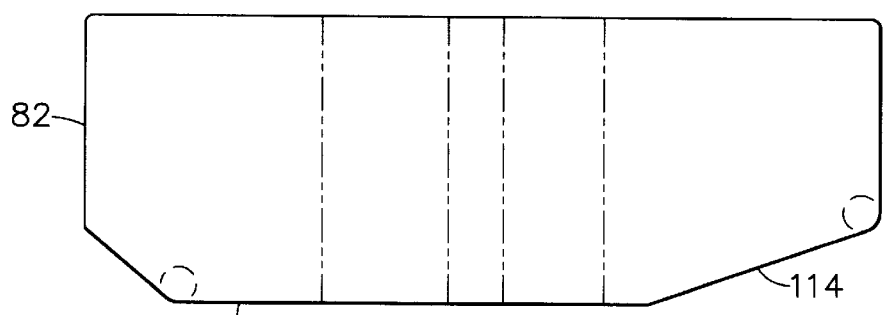
FIG. 4 is a side view of the cartridge of FIG. 1.
Figure 5:
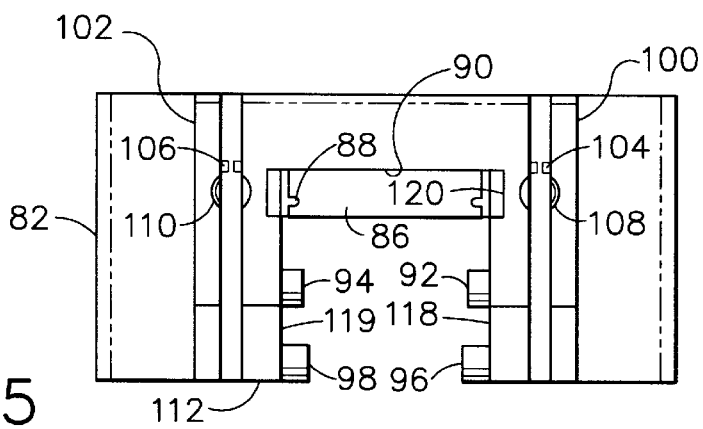
FIG. 5 is a distal end view of the cartridge of FIG. 1.
Figure 6:
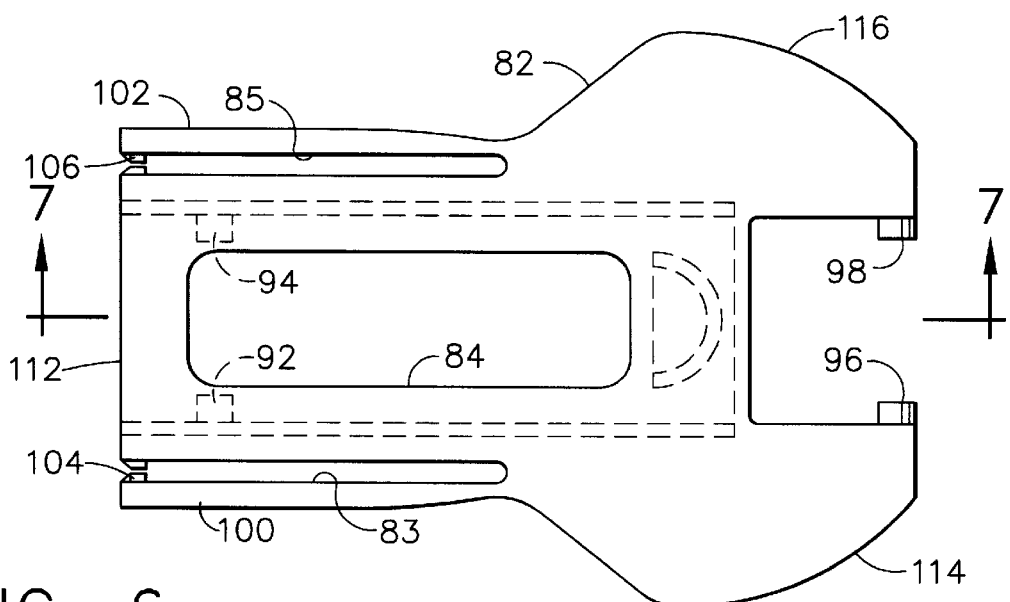
FIG. 6 is a top view of the cartridge of FIG. 1.

Referring now to FIGS. 4, 5, and 6, a frame 82 of the cartridge 80 is shown in three orthographic views. The frame 82 is preferably molded from a medical grade, rigid plastic and comprises a channel 112 configured to fit slidably onto the shaft 136 of the applicator 130 shown in FIG. 1. The frame 82 further comprises a left crimping beam 100 cantileverly attached to the channel 112 so as to form the left opening 83. Similarly, a right crimping beam 102 is cantileverly attached to the channel 112 so as to form the right opening 85. Recessed within the distal face 81 of the frame 82, and centered on the left and right openings, 83 and 85, are the left and right cavities, 108 and 110 respectively, provided for removeably retaining the left and right connectors, 50 and 52. A left hip 114 and a right hip 116 are widened portions of the frame 82 to facilitate grasping and pulling the cartridge 80 proximally on the shaft 136 of the applicator 130. The frame 82 has a first post 92, a second post 94, a third post 96, and a fourth post 98, for slidably retaining the frame 82 upon the shaft 136 of the applicator 130. Posts 92 and 96 project from a left inside face 118 of the channel 112. Posts 94 and 98 project from a right inside face 119 of the channel 112. Still referring back to FIG. 1 in combination with FIGS. 4, 5, 6, first post 92 slidably inserts into a left keyway 152 and is guided by a left ledge 156 which runs longitudinally along the shaft 136; second post 94 slidably inserts into a right keyway 150 and is guided by a right ledge 154 which runs longitudinally along the shaft 136, opposite the left ledge 156. Third post 96 slidably inserts into a left slot door 144 and is guided by a left longitudinal slot 148 running above and parallel to the left ledge 156. Fourth post 98 slidably inserts into a right slot door 142 and is guided by a right slot 146 that runs above and parallel to right ledge 154.

Still referring to FIGS. 4, 5, and 6, the frame 82 further comprises a left severing element 104 adjacent to the left cavity 108, and a right severing element 106 adjacent to the right cavity 110. The severing elements, 104 and 106, concentrate a high local stress on the left and right sutures, 34 and 36, just proximal to the left and right connectors, 50 and 52, when the frame 82 is squeezed by the operator as earlier described. By simultaneously pulling on the left and right excess suture portions, 74 and 76, while the frame 82 is squeezed, the excess suture portions, 74 and 76, can be severed at the severing elements, 108 and 106, while the connectors, 50 and 52, are attached to the suture filament 35. The severing elements, 104 and 106, may be molded-in projections of the cartridge frame 82, or separate, sharpened metallic components attached to the frame 82. A cartridge window 84 is provided in the frame 82 for viewing of the cable loop assembly 49 to facilitate mounting of the cartridge 80 onto the track 136 of the applicator 130. The window 84 also provides a convenient means for the operator to know if a cable loop assembly 49 is contained inside the cartridge 80.

Figure 7:
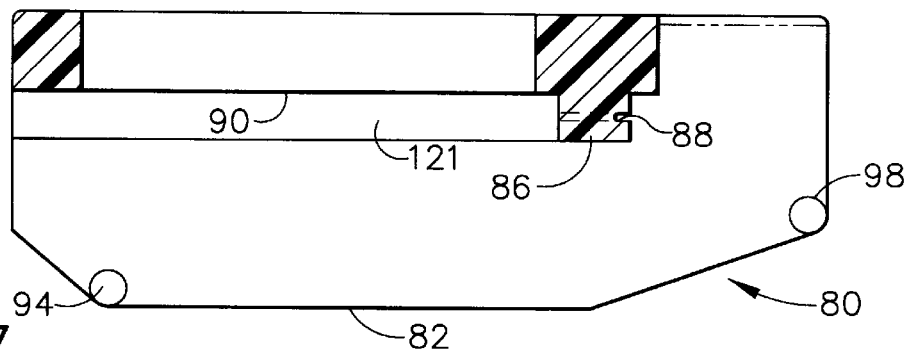
FIG. 7 is a sectional view of the cartridge, taken along line 7—7 of FIG. 6.
Figure 8:
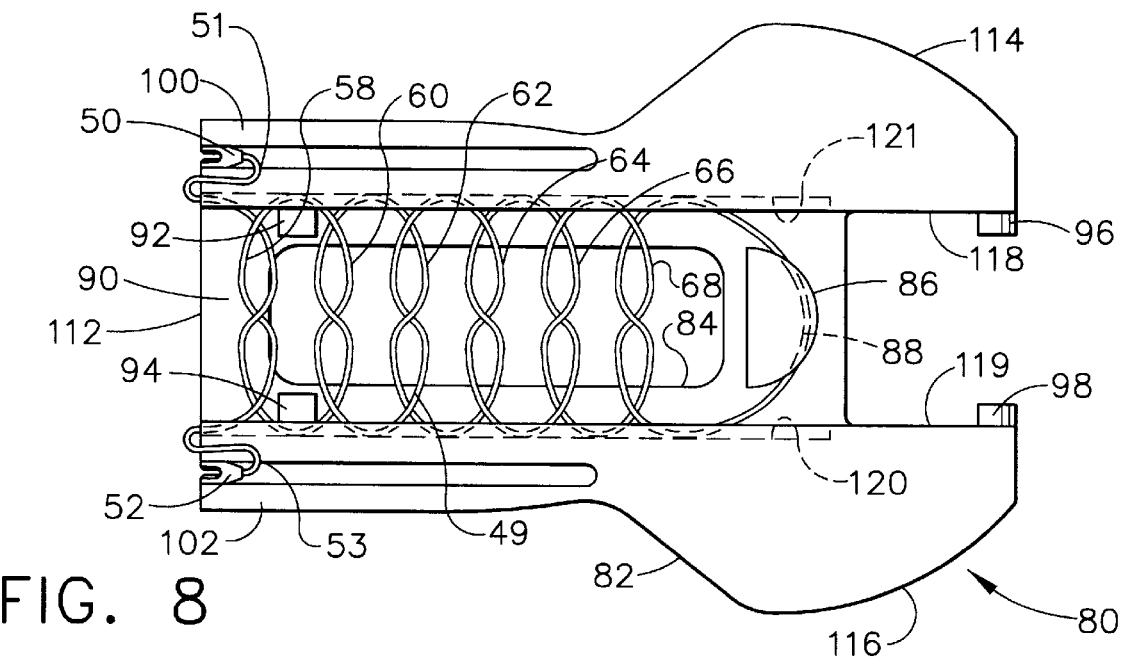
FIG. 8 is a bottom view of the cartridge of FIG. 1 assembled with a cable loop assembly having a pair of cone shaped suture connectors inserted into cavities in the distal face of the cartridge.
Figure 9:
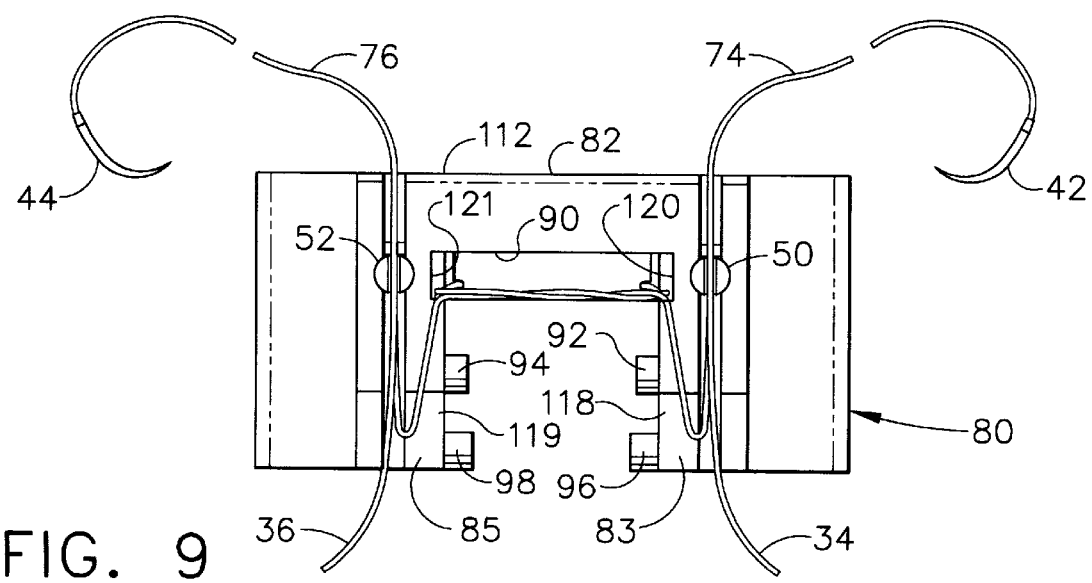
FIG. 9 is a view of the distal end of the cartridge shown in FIG. 8, and a suture having a needle attached to each of the two ends, and the suture is placed into the pair of suture connectors.

FIG. 7 is a sectional view of the cartridge 80 revealing a right recess 121 and a bight groove 88. FIG. 8 is a bottom view of the cartridge 80 containing the cable loop assembly 49 which is removeably retained in the left recess 120, the right recess 121, and the bight groove 88. FIG. 9 additionally shows the left and right sutures, 34 and 36, with their attached needles, 42 and 44, as they would appear when being placed into the left and right connectors, 50 and 52, of the cartridge 80. The cable loop assembly 49 is shown as it is contained inside the left and right recesses, 120 and 121, inside the channel 112. The cable material of the cable loop assembly 49 may be selected from, but is not limited to, a group including polyethylene, polypropylene, polyester, nickel-titanium alloy "memory metal", and braided stainless steel. The cable materials may be single filament or multi-filament. Common characteristics of the materials named are high flexibility and lubricity so that overhand knots loosely tied into the cable can be easily unraveled without the cable "kinking".

The cable loop assembly 49 comprises a plurality of loosely tied overhand loops: a first loop 58, a second loop 60, a third loop 62, a fourth loop 64, a fifth loop 66, and a proximal loop 68. These loops 58–68 may be of the right hand or left-hand type, depending on how the ends of the cable were crossed over each other when each loop was made. In the preferred embodiments the loops alternate in sequence between the left hand and the right hand type. When a left-hand loop is combined with a right hand loop, a square knot is formed. A series of six alternately formed loops will result in three square knots formed on top of each other. Surgeons for most surgical procedures, including heart valve repair procedures prefer this kind of knot.

The substantial stiffness of the material of the cable loop assembly 49 causes each of the loops 58-68 to tend to expand in size, thus helping to retain the cable loop assembly 49 in the recesses 120 and 121, and also serving to keep the loops 58–68 substantially coplanar. The proximal loop 68 is hooked over a semi-circular stake 86 which projects off a anterior channel face 90. The cable is tightly inserted into a groove 88 of the stake 86. The left and right cable ends, 46 and 48, are fixedly attached to the left and right connectors, 50 and 52. The cable ends, 46 and 48, are folded against the distal face 81 and within the openings, 83 and 85, as shown.

FIG. 10 shows an enlarged portion of the cartridge 80 for when the right suture 36 is inserted into the connector 52 as was described for FIGS. 2 and 3. In FIG. 11 the right crimping beam 102 is shown squeezed against the channel 112 so that the right connector 52 becomes crimped onto or attached to the right suture 36. The subsequent release of the crimping beam 102 allows the connector 52 to be easily pulled from the right cavity 110 of the cartridge 80.

Figure 12:
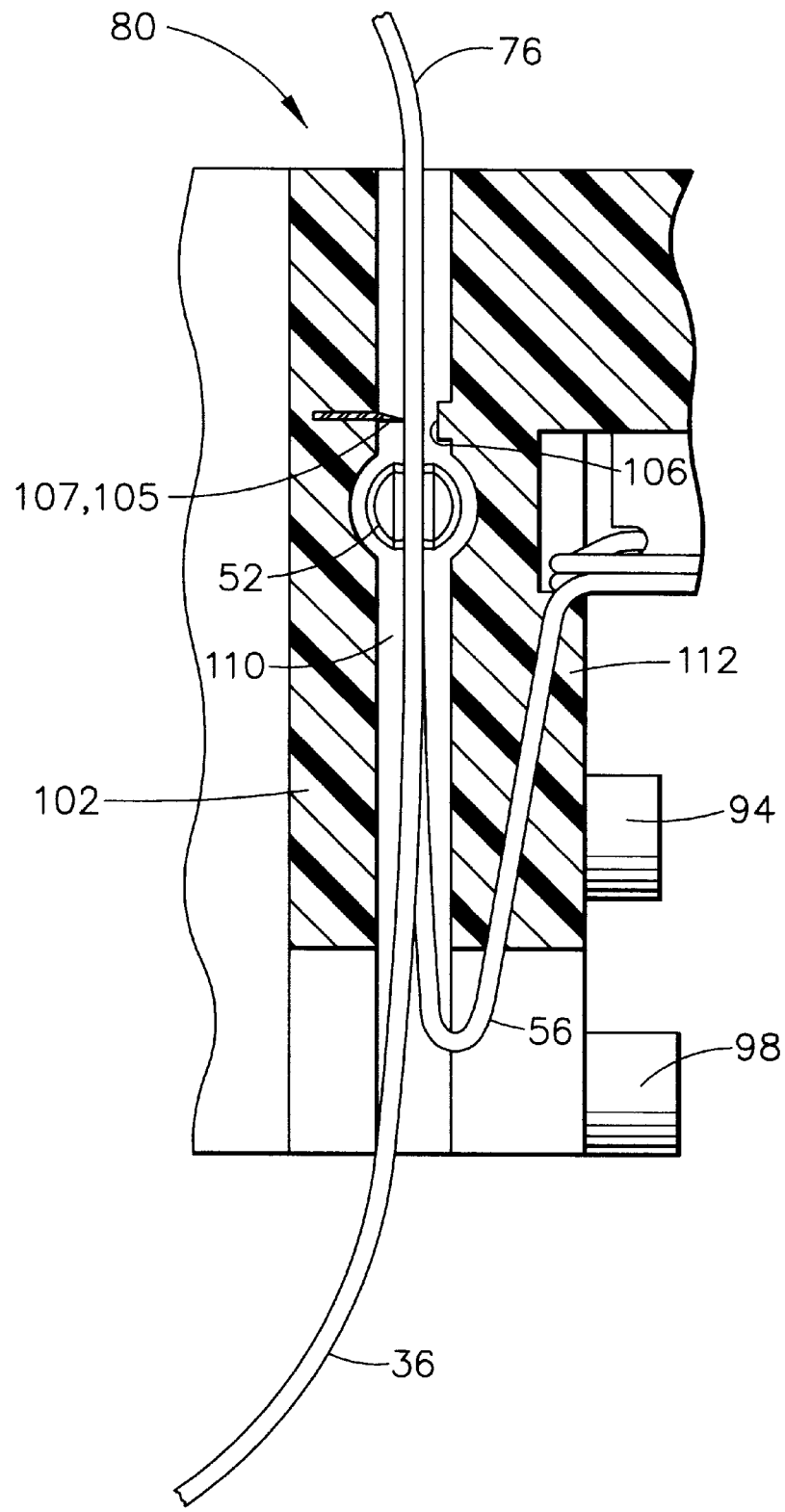
FIG. 12 is a sectional view of the cartridge taken along line 12—12 of FIG. 10, showing a suture cutter for removing the excess suture and needle.

FIG. 12 is an enlarged distal end view of the portion of the cartridge 80 shown in FIG. 10. The channel 112 is sectioned to show how right severing element 106 may include a sharp metal blade 107 which is attached to the crimping beam 102 so that the excess suture portion 76 is severed from the right suture 36 proximally to the connector 52.

Figure 13:
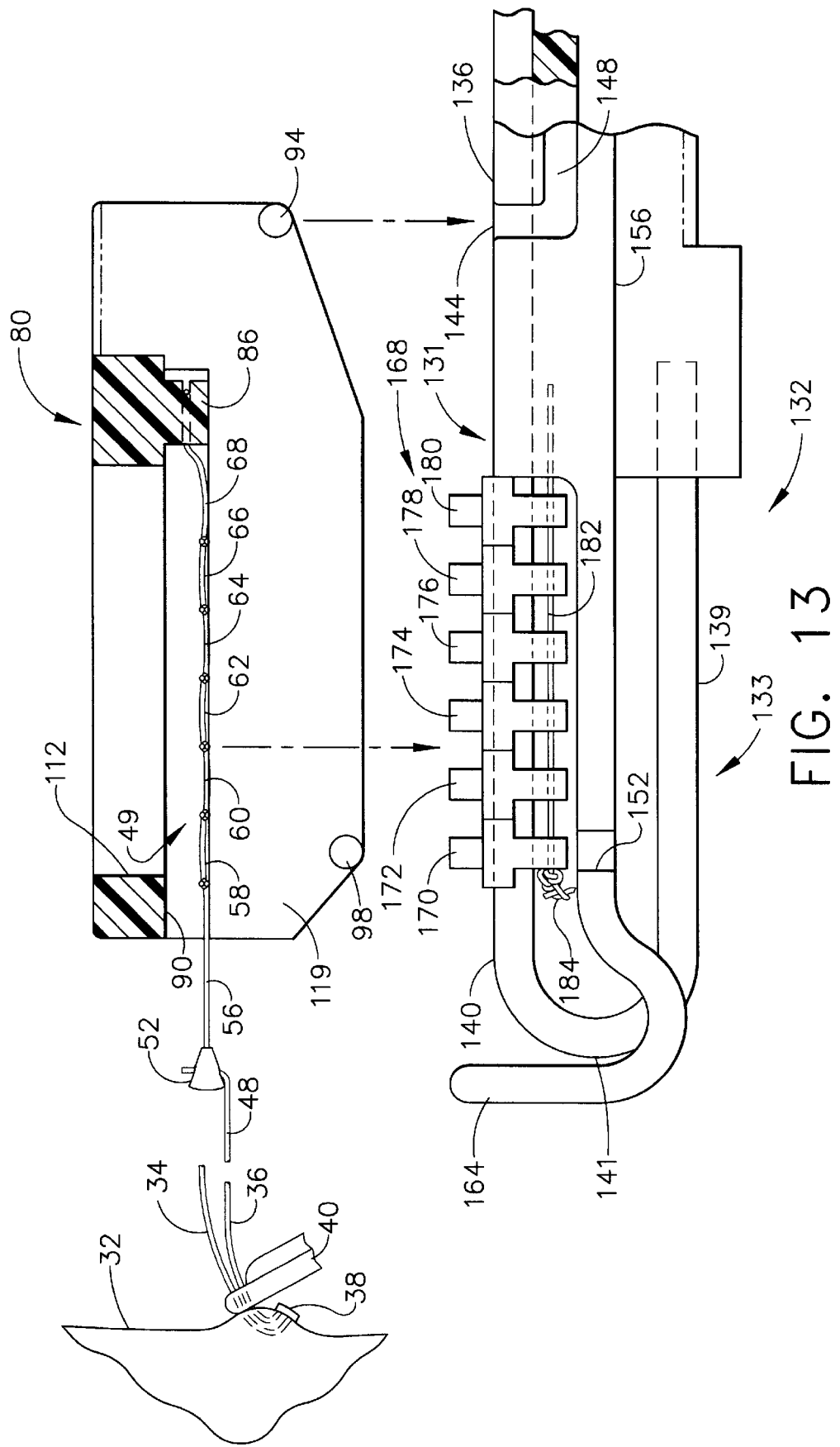
FIG. 13 is a side view in centerline section of the cartridge shown in FIG. 3, aligned for mounting onto the distal end portion of the applicator, also shown in FIG. 3.

FIG. 13 shows a side view of the cartridge 80 taken in longitudinal section as it is being aligned and lowered onto the track 136 of the applicator 130. The lug train 168 is slidably retained on the upper center rail 140. The upper center rail 140 is anchored on its proximal end to the shaft 136. The upper center rail 140 transitions on the distal end of the shaft 136 into a center rail bend 141 which transitions into the lower center rail 139 which finally is rigidly attached to the distal end 132 of the shaft 136. The upper and lower center rails define a vertical plane, which extends between the left and right prongs, 164 and 166.

The lug train 168 comprises a first lug 170, a second lug 172, a third lug 174, a fourth lug 176, a fifth lug 178, and a sixth lug 180. The number of lugs required is equal to the number of loops contained in the cable loop assembly 49 of the cartridge 80. Cartridges containing a different number of loops in the cable loop assembly 49 may be provided and would be used with an applicator 130 having a lug train 168 with a corresponding number of lugs. The individual lugs are held adjacent to one another by a lug tie 182 made from a flexible material such as braided polyester. A lug tie termination 184 is provided to retain the lug tie 182 in the lug train 168. The proximal portion of the lug tie 182 is attached to the distal end of the driver 138.

Figure 14:
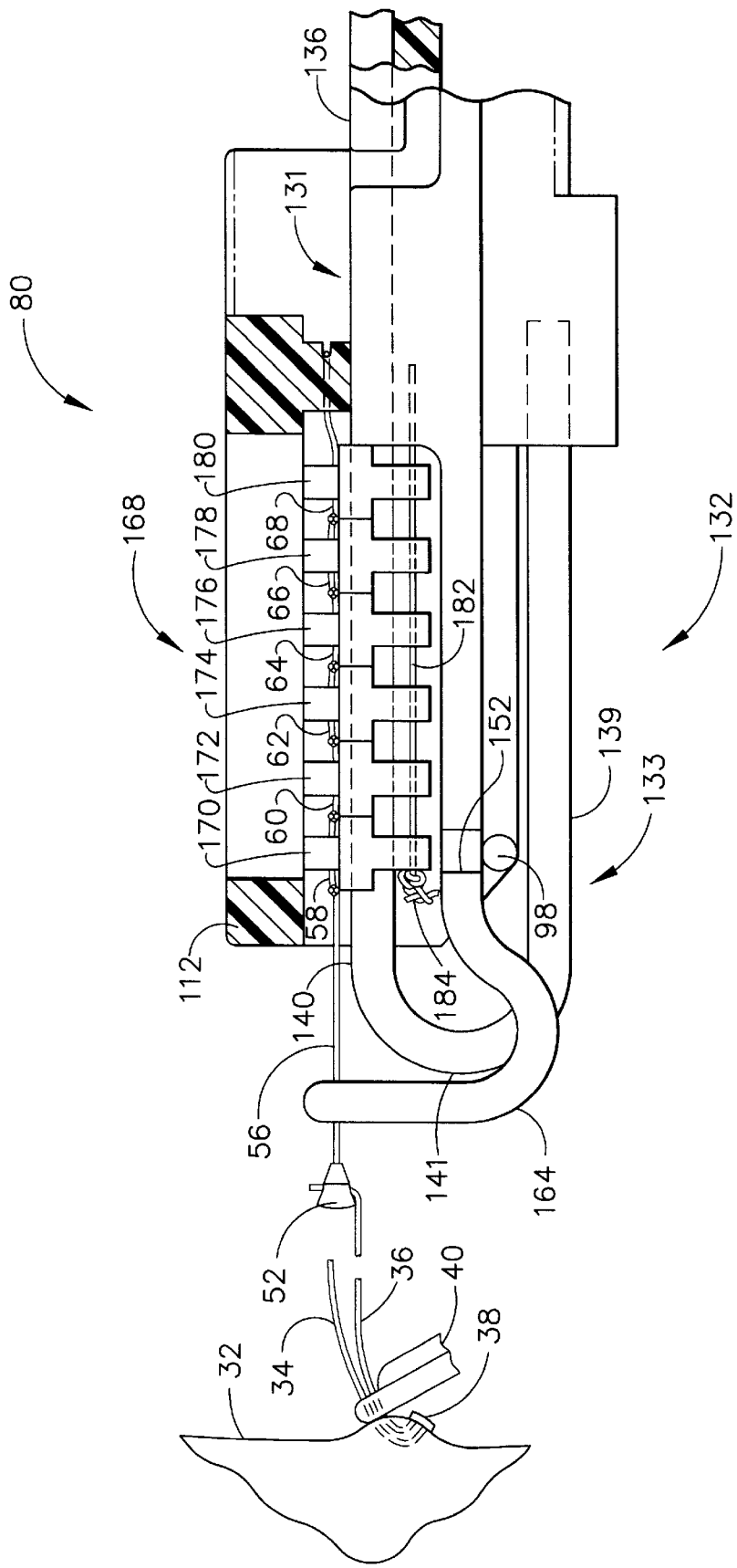
FIG. 14 is a side view in centerline section of the cartridge shown in FIG. 3, mounted onto the distal end portion of the applicator, also shown in FIG. 13.

In FIG. 13 the loops 58, 60, 62, 64, 66, and 68 of the cable loop assembly 49 are shown in alignment with their respective lugs 170, 172, 174, 176, 178, and 180 when the posts 94 and 98 are guided onto the shaft 136 as earlier described. During this step of mounting the cartridge 80 onto the applicator tool 130, the left and right sutures, 34 and 36, will have already been placed into the surgical patient and attached to the cartridge 80. FIG. 14 shows the cartridge mounted on the track 136 of the applicator 130 prior to actuation. The cable ends, 56 and 54, pass between the prongs, 164 and 166, and extend from the distal end 132 of the shaft 136.

FIG. 15 is a top view of the cartridge 80 as it is initially mounted on the shaft 136. The cartridge frame 82 is shown in phantom view in order to see how the individual loops 58, 60, 62, 64, 66, and 68 are loosely aligned onto the individual lugs 170, 172, 174, 176, 178, and 180. The distal end 137 of the driver 138 is abutted against the most proximal lug 180.

The driver 138 and the lug train 168 are sometimes referred to in combination as a pusher, for pushing the pre-tied loops, 58, 60, 62, 64, and 66, from the cable loop assembly 49 to the left and right sutures, 34 and 36.

FIG. 16 is a top view of the distal end of the applicator 130 after the cartridge 80 has been pulled by the hand of the operator in the proximal direction along the shaft 136 in order to transfer the cable loop assembly 49 to the lug train 168. The individual loops have tightened around the lugs, the proximal loop 68 has been extended in length, and the cable ends, 54 and 56, have straightened under tension due to the retraction of the cartridge 80.

Figure 17:
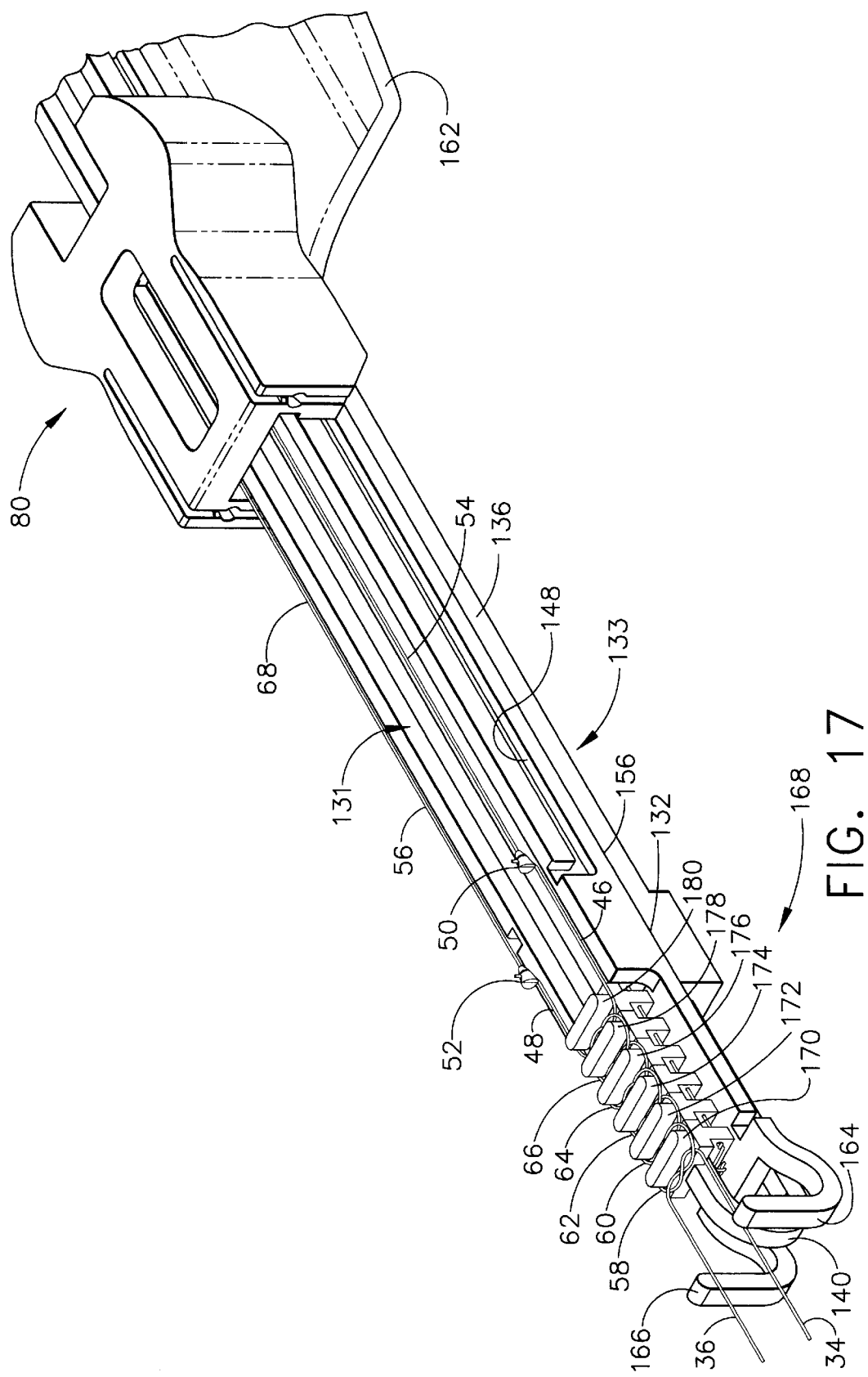
FIG. 17 is an isometric view of the applicator and cartridge after a plurality of suture throws has been transferred from the cable loop assembly to the suture.

FIG. 17 is an isometric view of part of the present invention as the cartridge 80 is further retracted in the proximal direction along the shaft 136. The operator's hands have been removed for clarity, but for this step, the operator would be using one hand to hold the grip of the applicator 130 while the other hand is used to grasp and pull the cartridge 80. In FIG. 17, the loops 58, 60, 62, 64, 66, 68 that were present in the cable shown in FIG. 16 have been transferred to the left and right sutures, 34 and 36. The loops 58, 60, 62, 64, and 66 have become, in essence, suture throws. Cable loop 68 has become further extended and is now comprised of left and right suture/cables, 46 and 48. Loop 68 eventually becomes the sixth suture throw. In order for the cable loops to be transferred to the left and right sutures, 34 and 36, the left and right connectors, 50 and 52, must pass through the spaces between the lugs, 170, 172, 174, 176, 178, and 180. The conical shape of the crimped connectors, 50 and 52, facilitate their movement through the serpentine path they must follow to "untie" the cable and pass back and forth between the lugs. This step may be accomplished as quickly as the operator can pull the cartridge 80 proximally along the shaft 136 in a controllable fashion.

Figure 18:
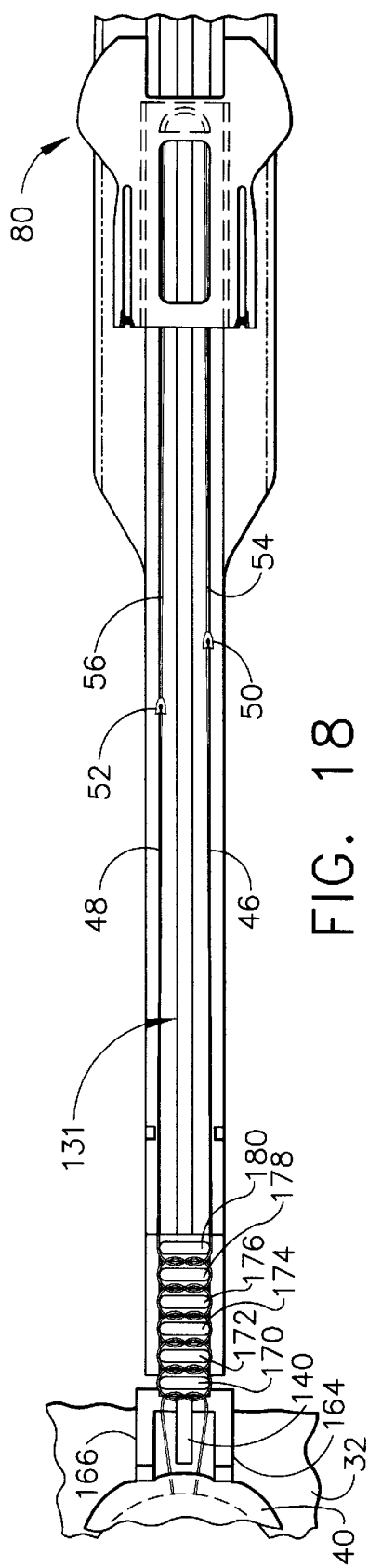
FIG. 18 is a top view of the applicator placed near the suture site in the surgical patient.
Figure 19:
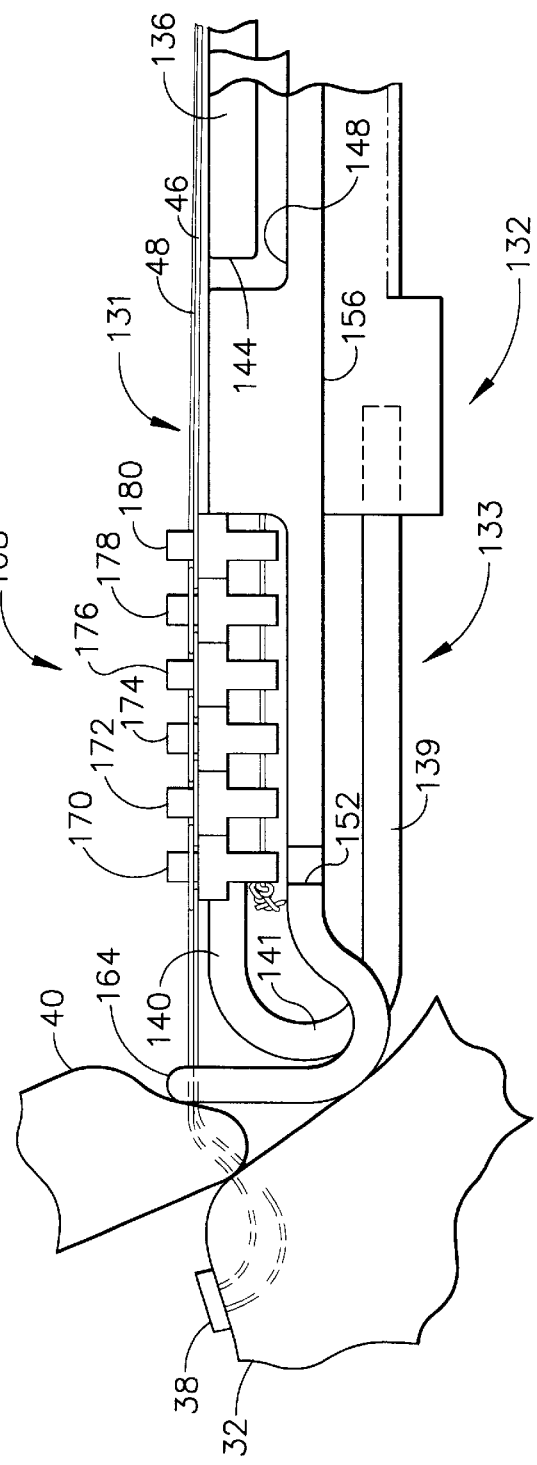
FIG. 19 is an enlarged side view of the distal end portion of the applicator shown in FIG. 18.

The next step in the sequence of operation of the present invention is shown in FIGS. 18 and 19. Here the operator moves the applicator 130 distally so that the tynes, 164 and 166, are brought up against the prosthesis 40, the desired destination for the completed knot. As the applicator 130 is being moved distally towards the patient, the operator pulls the cartridge 80 in the proximal direction along the shaft 136. This results in the suture throws 59, 61, 63, 65, 67, and 68 being brought near to the prosthesis 40. If the initial length of the left and right sutures, 34 and 36, was substantially longer than the length of the track 136, then it is necessary for the operator to continue to pull the cartridge 80 in the proximal direction and allow it to come off of the proximal end of the shaft 136. The operator then must continue to pull the cartridge 80 proximally while moving the prongs, 164 and 166, towards the prosthesis 40, being sure to maintain tension on the left and right suture/cables, 46 and 48, the entire time. The operator should also keep the suture/cables, 46 and 48, approximately parallel to the shaft 136 so that the throws, 59, 61, 63, 65, 67, and 68 do not come off of the tops of the lugs 170, 172, 174, 176, 178, 180 of the lug train 168. In this way the present invention is used much like a conventional knot pusher, well known in the surgical art, except that not one but a plurality of knots are pushed towards the surgical site simultaneously. When the prongs, 164 and 166, are all the way up against the prosthesis 40 and tension is maintained on the suture/cables, 46 and 48, so that the suture throws are still tightly wrapped around their respective lugs, then the actuator 160 may be actuated.

Figure 20:
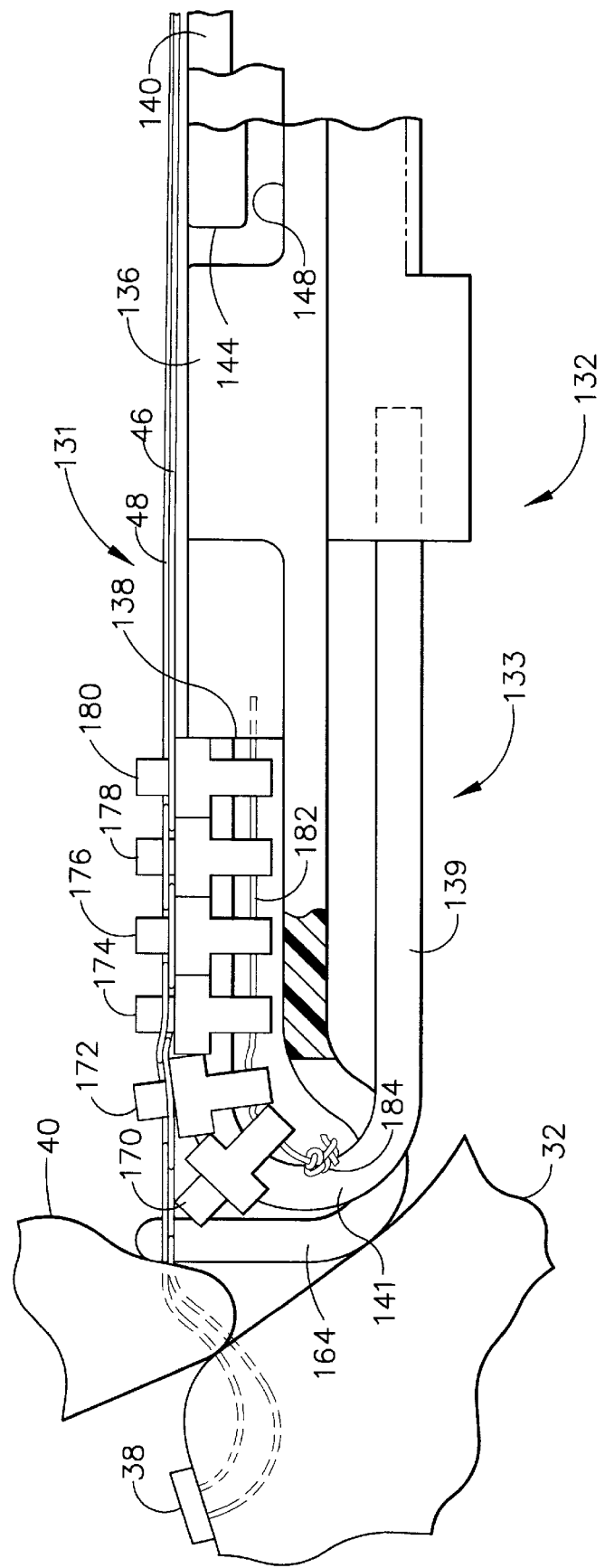
FIG. 20 is a side view of the distal end portion of the applicator as a first suture throw is released from a dispensing lug of the applicator.

FIG. 20 shows the distal end 132 of the present invention as the actuator 160 (see FIG. 3) is being actuated in order to deploy the suture throws 59, 61, 63, 65, 67, and 68 to their final destination against the prosthesis 40. When the actuator 160 is initially actuated, the driver 138 moves in the distal direction and pushes the lug train 168 distally along the upper center rail 140. As the first lug 170 is pushed around the center rail bend 141, the first suture throw 59 comes off the first lug and adjacent to the prosthesis 40. As this occurs, the operator continues to pull back on the cartridge 80 to maintain tension on the suture/cables, 46 and 48, as described for FIG. 18. This results in the first throw 59 tightening against the prosthesis 40. As the actuator is further actuated, the remaining suture throws are likewise deployed and tightened upon the preceding throw. Only one complete actuation of the actuator 160 is necessary to deploy all the suture throws to their final location against the prosthesis 40. The "spent" lugs continue on their path around the center rail bend 141 and to the lower center rail 142 as the succeeding, "unspent" lugs move into position to deploy their respective suture throws. This sequence of deploying throws occurs as fast as the operator desires since the operator squeezing the actuator 160 controls actuation. The excess suture may then be trimmed a safe distance from the knot using a scalpel or surgical scissors. Release of the actuator 160 causes it to return to its initial position as shown in FIG. 3, returning the driver 138 and the lug train 168 to their initial positions also. The applicator tool 130 is then ready for use with another cartridge 80 containing a cable loop assembly 49.

FIG. 21 is an isometric view of the distal end 132 of the track 136 of the present invention, with the lug train 168 removed for clarity. The center rail elements 140, 141, and 142 are preferably made from a continuous, square, stainless steel rod. The tynes, 164 and 166, are preferably molded integrally with the track 136 from a rigid, medical grade plastic such as polycarbonate. The prongs, 164 and 166, may also be made, however, from a stainless steel and rigidly affixed to the shaft 136 by any one of numerous methods well known to those skilled in the art.

FIGS. 22, 23, and 24 are views of the first lug 170, which is identical to the other lugs 172, 174, 176, 178, and 180. The first lug 170 comprises an upper portion 177, a middle portion 179, a lower portion 183, a center rail journal 171, and a pair of lug tie holes, 173 and 175. The lugs are preferably molded from a rigid, medical grade plastic such as polycarbonate.

Figure 25:
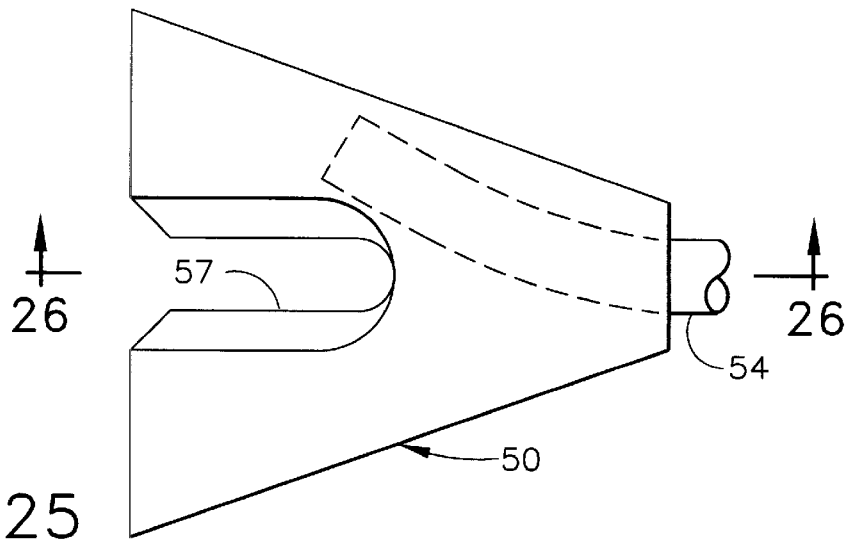
FIG. 25 is a top view of the connector of FIG. 2.
Figure 26:
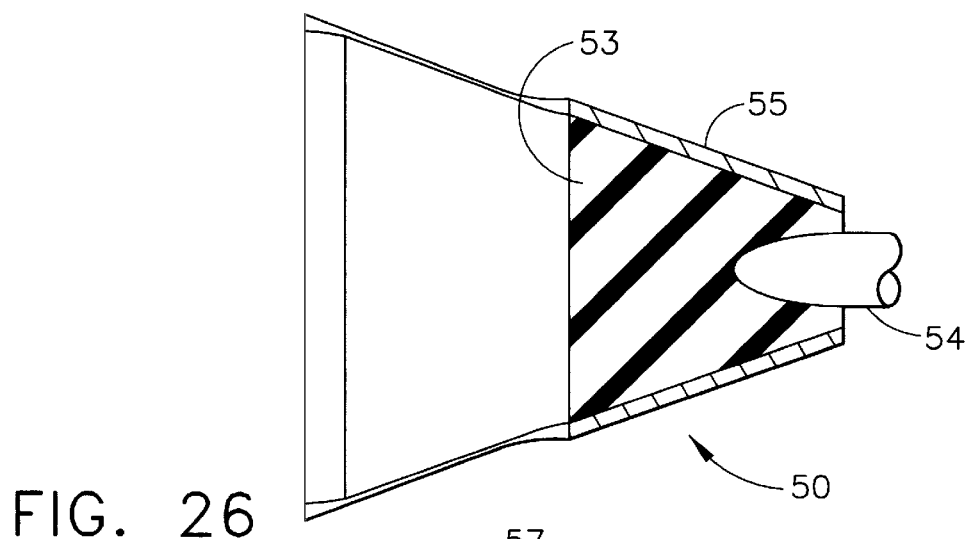
FIG. 26 is a side view in centerline section of the connector shown in FIG. 25, taken along line 26—26.
Figure 27:
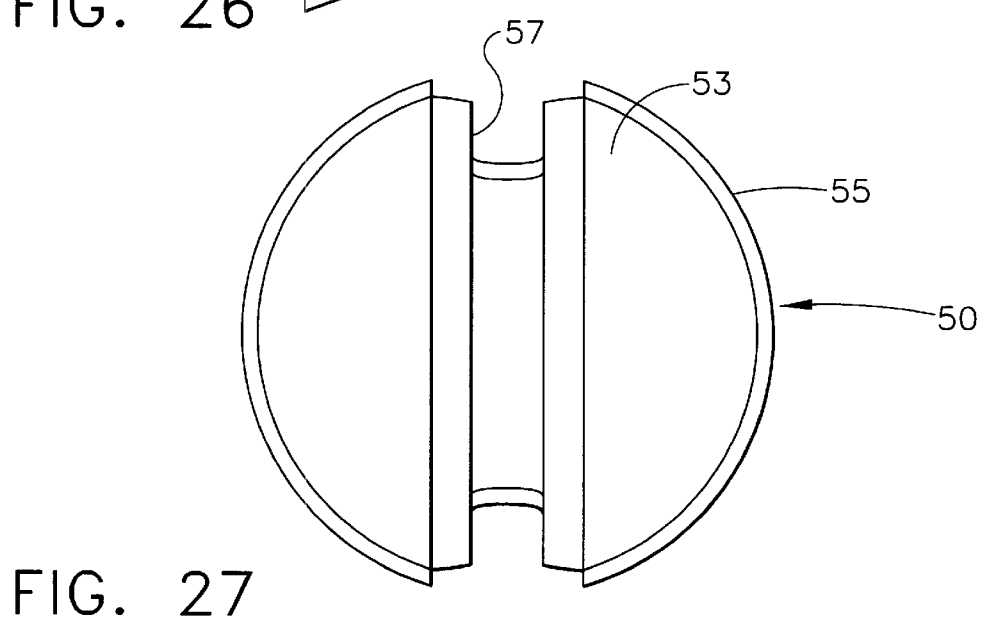
FIG. 27 is a distal end view of the connector shown in FIG. 25.

FIGS. 25, 26, and 27 show views of the left connector 50 before it is crimped onto the left suture 34. In this preferred embodiment, the connector 50 comprises a deformable casing 55 and a plastic or rubber filler 53, also referred to as a compliant insert. The deformable casing 55 is preferably made of a stainless steel. The end of the cable 54 and the casing 50 may be insert molded with the filler 53. A slot 57 is provided for receiving the left suture 34. In a second embodiment, the plastic filler 53 and the cable 54 may be integrally molded as one piece, and the casing 55 assembled onto it afterwards.

Figure 28:
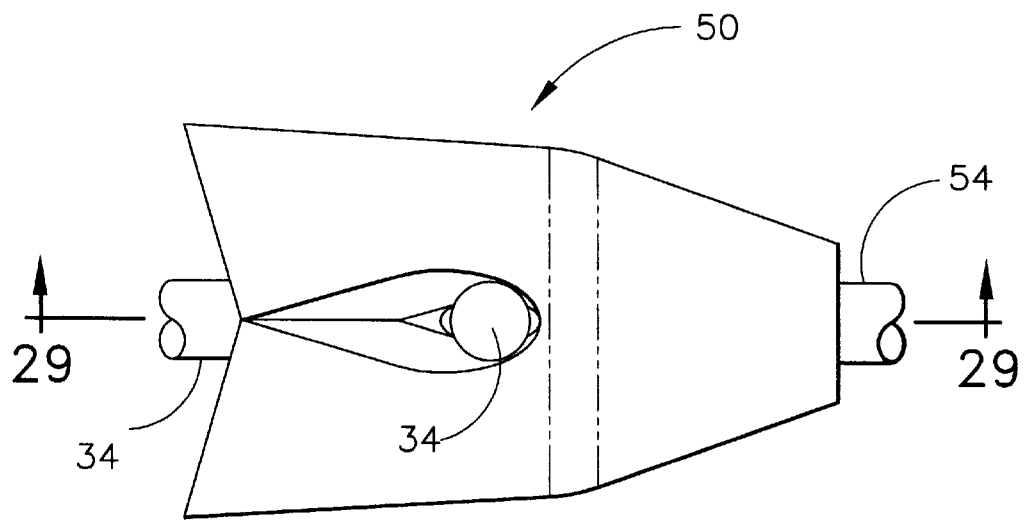
FIG. 28 is a top view of the connector shown in FIG. 25, after the connector has been closed onto a suture.
Figure 29:
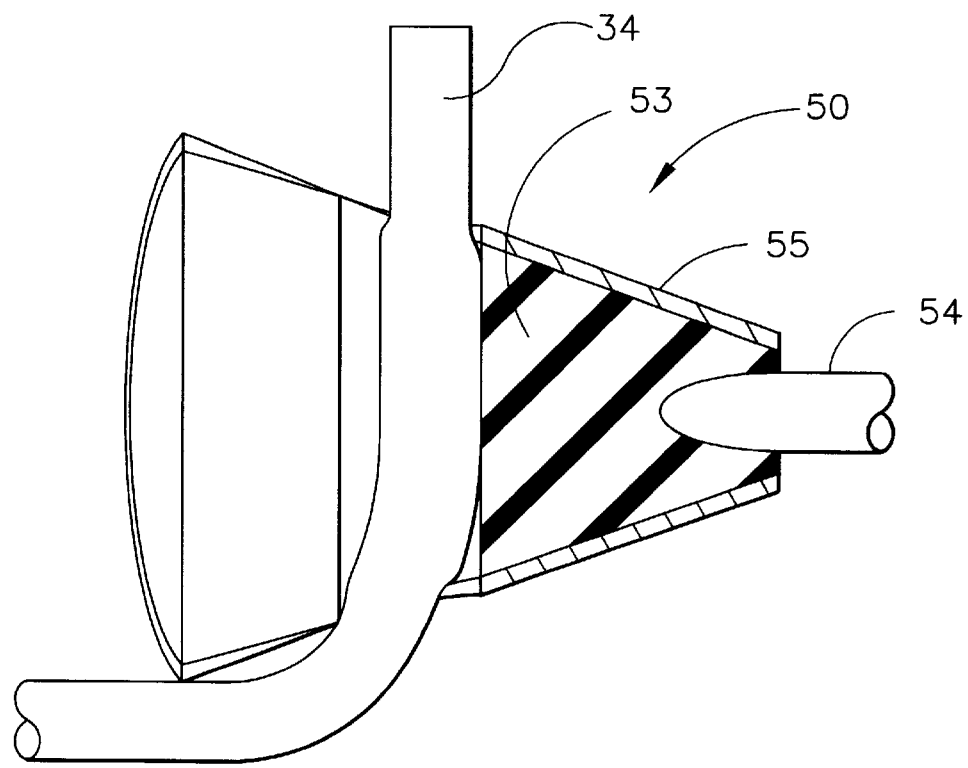
FIG. 29 is a side view in centerline section of the connector shown in FIG. 28, taken along line 29—29.

FIG. 28 shows the left connector 50 of FIGS. 25–27 after it has been crimped onto the left suture 34, as set forth in the steps described for FIGS. 10 and 11. FIG. 29 is a cross-sectional view of the left connector 50 after it has been crimped onto the left suture 34.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A surgical instrument for tying together two free suture ends of a suture filament placed into a surgical patient, said surgical instrument comprising:
   a. a handle having an actuator attached thereto;
   b. an elongated shaft attached to said handle, said shaft having a proximal end attached to said handle and a distal end extending therefrom;
   c. a cartridge removeably attached to said shaft, said cartridge comprising a cable, said cable having a proximal end secured to said cartridge and two free cable ends extending therefrom, each of said free cable ends having a suture connector attached thereto, said cable having a plurality of pre-tied loops disposed proximal to said free cable ends; and
   d. a pusher slideably disposed on said shaft, said pusher for transferring said pre-tied loops distally from said cable to said two free suture ends of said suture filament.

2. The surgical instrument of claim 1 wherein said pusher comprises a lug train and a driver, said lug train having a plurality of lugs equal in number to said plurality of said loops, said lugs flexibly attached to each other in a row and slideably attached to said distal end of said shaft, each lug having one of said loops operationally positioned on said lug when said cartridge is slideably attached to said shaft, said lug train operationally engaged to said driver, whereby actuation of said actuator causes said driver to move said lug train distally along a top surface of said shaft, around said distal end of said shaft, and then proximally along a bottom surface of said shaft, whereby said loops are released from said distal end of said instrument.

3. The surgical instrument of claim 1 wherein said cartridge comprises a frame having at least one projection for the slideable insertion into a longitudinal slot of said shaft, whereby said frame is moveable from said distal end to said proximal end of said shaft, for transferring said loops from said cable to said two free suture ends of said suture filament.

4. The surgical instrument of claim 1 further comprising at least one prong attached to and extending from said distal end of said shaft, said prong extending distally to said pusher.

5. The surgical instrument of claim 1 wherein said cartridge further comprises a pair of severing elements for severing excess suture portions proximal to any of said connectors when a suture is attached thereto.

6. The surgical instrument of claim 1 wherein said cartridge further comprises a window for viewing said cable.

7. The surgical instrument of claim 1 wherein said actuator comprises a lever pivotally attached to said handle.

8. The surgical instrument of claim 1 wherein said cable is composed of a material selected from a group consisting of polyethylene, polypropylene, polyester, stainless steel, and nickel-titanium alloy.

9. The surgical instrument of claim 1 wherein each of said connectors comprises a compliant insert attached to an end of said cable, said compliant insert surrounded by a deformable casing, said compliant insert and said deformable casing having a connector slot for receiving one of said two free suture ends.

10. The surgical instrument of claim 9 wherein said cartridge further comprises a pair of crimping beams for manually crimping said connectors to said two free suture ends received in said connector slots.

11. A cartridge for use with a surgical instrument for tying together two free ends of a suture filament placed into a surgical patient, said cartridge comprising:
   a. a frame having proximal and distal ends, said frame including a device for attaching said cartridge to a surgical instrument; and
   b. a cable disposed within said frame, said cable having a proximal end secured to said cartridge and two free cable ends extending therefrom, said cable having a plurality of pre-tied loops proximal to said two free ends, each of said free ends of said cable having a suture connector attached thereto.

12. The cartridge of claim 11 wherein said suture connectors have a connector slot for receiving one of said two free ends of a suture filament.

13. The cartridge of claim 11 further comprising a window for viewing said cable.

14. The cartridge of claim 11 further comprising a pair of severing elements, for severing excess suture portions proximal to said connectors.

15. A surgical instrument for tying together two free suture ends of a suture filament placed into a surgical patient, said surgical instrument comprising:
   a. a handle having an actuator attached thereto;
   b. an elongated shaft attached to said handle, said shaft having a proximal end attached to said handle and a distal end extending therefrom;
   c. a cartridge removeably attached to said shaft, said cartridge comprising a cable, said cable having a proximal end secured to said cartridge and two free cable ends extending therefrom, each of said free cable ends having a suture connector attached thereto, said cable having a plurality of pre-tied loops disposed proximal to said free cable ends; and d. a pusher slideably disposed on said shaft, said pusher moves distally for transferring said pre-tied loops distally from said cable to said two free suture ends of said suture filament.

16. The surgical instrument of claim 15 wherein said pusher comprises a lug train and a driver, said lug train having a plurality of lugs equal in number to said plurality of said loops, said lugs flexibly attached to each other in a row and slideably attached to said distal end of said shaft, each lug having one of said loops operationally positioned on said lug when said cartridge is slideably attached to said shaft, said lug train operationally engaged to said driver, whereby actuation of said actuator causes said driver to move said lug train distally along a top surface of said shaft, around said distal end of said shaft, and then proximally along a bottom surface of said shaft, whereby said loops are released from said distal end of said instrument.

17. The surgical instrument of claim 15 wherein said cartridge comprises a frame having at least one projection for the slideable insertion into a longitudinal slot of said shaft, whereby said frame is moveable from said distal end to said proximal end of said shaft, for transferring said loops from said cable to said two free suture ends of said suture filament.

18. The surgical instrument of claim 15 further comprising at least one prong attached to and extending from said distal end of said shaft, said prong extending distally to said pusher.

19. The surgical instrument of claim 15 wherein said cartridge further comprises a pair of severing elements for severing excess suture portions proximal to any of said connectors when a suture is attached thereto.

20. The surgical instrument of claim 15 wherein said cartridge further comprises a window for viewing said cable.

21. The surgical instrument of claim 15 wherein said actuator comprises a lever pivotally attached to said handle.

22. The surgical instrument of claim 15 wherein said cable is composed of a material selected from a group consisting of polyethylene, polypropylene, polyester, stainless steel, and nickel-titanium alloy.

23. The surgical instrument of claim 15 wherein each of said connectors comprises a compliant insert attached to an end of said cable, said compliant insert surrounded by a deformable casing, said compliant insert and said deformable casing having a connector slot for receiving one of said two free suture ends.

* * * * *